(12) United States Patent
Reichert et al.

(10) Patent No.: US 6,258,815 B1
(45) Date of Patent: Jul. 10, 2001

(54) SPECIFIC IMMUNOPHILIN LIGANDS AS ANTIASTHMATICS AND IMMUNOSUPPRESSANTS

(75) Inventors: Dietmar Reichert, Eschau; Bernhard Kutscher, Maintal; Holger Bang, Erlangen; Kay Brune, Marloffstein; Gerhard Quinkert, Glashütten; Hans-Günter Schaible, Bruchköbel, all of (DE)

(73) Assignee: ASTA Medica Aktiengesellschaft (DE)

( * ) Notice: Subject to any disclaimer, the term of this patent is extended or adjusted under 35 U.S.C. 154(b) by 0 days.

(21) Appl. No.: 08/847,639

(22) Filed: Apr. 25, 1997

(30) Foreign Application Priority Data

Apr. 25, 1996 (DE) .............................. 196 16 509

(51) Int. Cl.[7] .......................... A01N 43/54; A01N 43/40; C07D 104/06; C07D 403/06
(52) U.S. Cl. .......................... 514/253; 514/323; 514/397; 514/414; 544/106; 544/238; 548/312; 548/468; 548/490; 546/201
(58) Field of Search .................... 548/490, 312, 548/468; 544/106, 238; 546/201; 514/323, 253, 414, 397

(56) References Cited

U.S. PATENT DOCUMENTS

| | | | |
|---|---|---|---|
| 4,725,581 | 2/1988 | Vincent et al. | 514/18 |
| 4,983,623 | 1/1991 | Henning et al. | 514/414 |
| 5,296,732 | 3/1994 | Vincent et al. | 257/565 |
| 5,384,322 | 1/1995 | Vincent et al. | 514/249 |
| 5,506,237 | 4/1996 | De Nanteuil et al. | 514/299 |
| 5,547,978 | 8/1996 | Christensen et al. | 514/422 |

FOREIGN PATENT DOCUMENTS

| | | |
|---|---|---|
| 25334/92 | 4/1993 | (AU) . |
| 0 320 753 | 12/1988 | (EP) . |
| 0320753A2 | 6/1989 | (EP) . |
| 2681864 | 4/1993 | (EP) . |
| 0 618 193 | 10/1994 | (EP) . |
| 0618193A1 | 10/1994 | (EP) . |
| 2585709 | 2/1987 | (FR) . |

OTHER PUBLICATIONS

"Preparation of pyrrolidin–2–ylcarbonylheterocyclic compound derivatives as prolylendopeptidase inhibitors," Chemical Abstracts, vol. 123, 1995, p. 1356.

Bernard Portevin, et al., "New Prolyl Endopeptidase Inhibitors: In Vitro and in Vivo Activities of Azabicyclo[2.2.2] octane, Azabicyclo[2.2.1]heptane, and Perhydroindole Derivatives", Journal of Medicinal Chemistry, Jun. 7, 1996, pp. 2379–2391, XP002036250.

Chemical Abstracts, vol. 123, No. 11, Sep. 11, 1995,abstract No. 144641r, XP002036251, siehe Zusammenfassung.

M. Bodansky, "Principles of Peptide Synthesis", Chapt. III. "Reversible Blocking Of Amino and Carboxyl Groups", Springer–Verlag, 1984, pp. 82–118.

John M. Stewart, et al., "Solid Phase Peptide Synthesis", 2d Ed. Chapt. 1, "The Chemistry of Solid Phase Peptide Synthesis", Pierce Chemical Company, Rockford, Il., pp. 1–62, 1995.

*Primary Examiner*—Joseph Mckane
*Assistant Examiner*—Dominic Keating
(74) *Attorney, Agent, or Firm*—Cushman Darby & Cushman

(57) ABSTRACT

The novel specific immunophilin ligands of the general formula I have an antiasthmatic and immunosuppressive action and are suitable for the preparation of drugs.

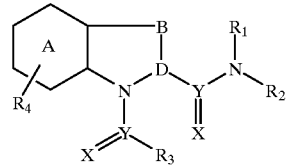

28 Claims, 1 Drawing Sheet

SPECIFIC IMMUNOPHILIN LIGANDS AS ANTIASTHMATICS AND IMMUNOSUPPRESSANTS

BACKGROUND OF THE INVENTION

Field of the Invention

The invention relates to novel specific immunophilin ligands of the formula

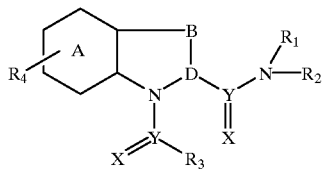

I

The radicals $R_1$, $R_2$, $R_3$, $R_4$, X, Y, A, B and D are defined as follows:

$R_1$ is hydrogen, a $(C_1-C_{12})$-alkyl group or a $(C_2-C_6)$-alkoxy group, where the alkyl group is linear or branched and can be substituted by a monocyclic or bicyclic heteroaryl having 1–4 heteroatoms, preferably N, S or O, such as morpholine, piperazine, piperidine, indole, indazole, phthalazines, thiophene, furan or imidazole, or monosubstituted or polysubstituted by a phenyl ring. This phenyl ring can itself be monosubstituted or polysubstituted by halogen, $(C_1-C_6)$-alkyl, $(C_3-C_7)$-cycloalkyl, carboxyl groups, carboxyl groups esterified with linear or branched $(C_1-C_6)$-alkanols, carbamoyl groups, trifluoromethyl groups, hydroxyl groups, methoxy groups, ethoxy groups, benzyloxy groups or amino groups, which in turn are substituted by benzyl, benzoyl or acetyl.

$R_1$ can also be the amine radical of the methyl esters of the following amino acids: histidine, leucine, valine, serine (Bzl), threonine, pipecolic acid, piperidine-4-carboxylic acid, piperidine-3-carboxylic acid, ε-NH$_2$-lysine, ε-Z-NH-lysine, ε-(2Cl-Z)-NH-lysine, 2-pyridylalanine, phenylalanine, tryptophan, glutamic acid, arginine (Tos), asparagine, citrulline, homocitrulline, ornithine, proline, indoline-2-carboxylic acid, octahydroindolinecarboxylic acid, tetrahydroisoquinolinecarboxylic acid, 5-aminovaleric acid and 8-aminooctanoic acid.

$R_2$ is hydrogen, a $(C_1-C_{12})$-alkyl group or a $(C_2-C_6)$-alkoxy group, where the alkyl group is linear or branched and can be substituted by a monocyclic or bicyclic heteroaryl having 1–4 heteroatoms, preferably N, S or O, such as morpholine, piperazine, piperidine, indole, indazole, phthalazines, thiophene, furan or imidazole, or monosubstituted or polysubstituted by a phenyl ring. This phenyl ring can itself be monosubstituted or polysubstituted by halogen, $(C_1-C_6)$-alkyl, $(C_3-C_7)$-cycloalkyl, carboxyl groups, carboxyl groups esterified with linear or branched $(C_1-C_6)$-alkanols, carbamoyl groups, trifluoromethyl groups, hydroxyl groups, methoxy groups, ethoxy groups, benzyloxy groups or amino groups, which in turn are substituted by benzyl, benzoyl or acetyl.

$R_3$ is hydrogen, butoxycarbonyl, carboxybenzyl, mono-, bi- or tri-cyclic carbonylaryl or carbonylheteroaryl having 1–4 heteroatoms, preferably N, S or O, where aryl or heteroaryl itself can be monosubstituted or polysubstituted by halogen, $(C_1-C_6)$-alkyl, $(C_3-C_7)$-cycloalkyl, carboxyl groups, carboxyl groups esterified with linear or branched $(C_1-C_6)$-alkanols, carbamoyl groups, trifluoromethyl groups, hydroxyl groups, methoxy groups, ethoxy groups, benzyloxy groups or amino groups, which in turn are substituted by benzyl, benzoyl or acetyl. $R_3$ can also be; carboxy-$(C_1-C_6)$-alkyl, where the alkyl group can be linear or branched and can be substituted by a monocyclic or bicyclic heteroaryl having 1–4 heteroatoms, preferably N, S or O, such as morpholine, piperazine, piperidine, indole, indazole, phthalazines, thiophene, furan or imidazole, or monosubstituted or polysubstituted by a phenyl ring, where this phenyl ring itself can be monosubstituted or polysubstituted by halogen, $(C_1-C_6)$-alkyl, $(C_3-C_7)$-cycloalkyl., carboxyl groups, carboxyl groups esterified with linear or branched $(C_1-C_6)$-alkanols, carbamoyl groups, trifluoromethyl groups, hydroxyl groups, methoxy groups, ethoxy groups, benzyloxy groups or amino groups, which in turn are substituted by benzyl, benzoyl or acetyl.

$R_3$ can also be the acid radical of the following amino acids: histidine, leucine, valine, serine (Bzl), threonine, pipecolic acid, piperidine-4-carboxylic acid, piperidine-3-carboxylic acid, ε-NH$_2$-lysine, ε-Z-NH-lysine, ε-(2Cl-Z)-NH-lysine, 2-pyridylalanine, phenylalanine, tryptophan, glutamic acid, arginine (Tos), asparagine, citrulline, homocitrulline, ornithine, proline, indoline-2-carboxylic acid, octahydroindolinecarboxylic acid, tetrahydroisoquinolinecarboxylic acid, 5-aminovaleric acid and 8-aminooctanoic acid, where the N terminus of the amino acids can be substituted by butoxycarbonyl, carboxybenzyl or the acid radical of mono-, bi- or tri-cyclic arylcarboxylic or heteroarylcarboxylic acids having 1–4 heteroatoms, preferably N, S or O, such as methoxyphenylacetic acid, naphthylacetic acid, pyridylacetic acid, quinazolinonylacetic acid, indazolylacetic acid, indolylglyoxylic acid, phenylglyoxylic acid, isobutylglyoxylic acid and 2-aminothiazole-4-glyoxylic acid, or by carboxy-$(C_1-C_{12})$-alkyl, carboxycyclopentane, carboxycyclohexane or benzoyl, which can be monosubstituted or polysubstituted by halogen, methoxy groups, amino groups, carbamoyl groups, trifluoromethyl groups, carboxyl groups or carboxyl groups esterified with linear or branched $(C_1-C_6)$-alkanols.

$R_4$ is H, F or $OR_5$.

$R_5$ is hydrogen, $(C_3-C_7)$-cycloalkyl, $(C_1-C_6)$-alkyl or carboxy-$(C_1-C_6)$-alkyl, where the alkyl group can be linear or branched and can be substituted by a mono-, bi- or tri-cyclic carbonylaryl or carbonylheteroaryl having 1–4 heteroatoms, preferably N, S or O, where aryl or heteroaryl itself can be monosubstituted or polysubstituted by halogen, $(C_1-C_6)$-alkyl, $(C_3-C_7)$-cycloalkyl, carboxyl groups, carboxyl groups esterified with linear or branched $(C_1-C_6)$-alkanols, carbamoyl groups, trifluoromethyl groups, hydroxyl groups, methoxy groups, ethoxy groups, benzyloxy groups or amino groups, which in turn are substituted by benzyl, benzoyl or acetyl.

A is aromatic, non-aromatic, aromatic/heterocyclic having 1–2 heteroatoms, preferably N, S or O, or non-aromatic/heterocyclic having 1–2 heteroatoms, preferably N, S or O.

B is $CH_2$.

D is CH.

B—D is CH=C.

X is O, S or $H_2$.

Y is C or a single bond.

The invention further relates to the biocompatible salts of the compounds of the formula I, to the processes for the preparation of the compounds of the formula I and to their use in pharmaceutics.

2. Background Information

Cyclosporin A (CsA) and FK 506 are immunosuppressive natural substances derived from fungi, which inhibit the $Ca^{2+}$-dependent signal transmission pathway in some types of cells. In T cells both agents inhibit the transcription of a number of genes, including the IL-2 gene, which is activated by stimulation of the T cell receptors (TCR). FK 506 and CsA both bind with high affinity to soluble receptor proteins (G. Fischer et al., *Nature* 337, 476–478, 1989; M. W. Harding et al., *Nature* 341, 755–760, 1989). The FK 506 receptor and the CsA receptor have been called FKBP and cyclophilin (Cyp) respectively. Both proteins catalyse the isomerization of cis and trans amide bond rotamers of peptides and are also frequently called immunophilins.

The CsA-Cyp or FK 506-FKBP supermolecule binds calcineurin (CN) and inhibits its phosphatase activity. The cytosolic phosphorylated component of the transcription factor NF-AT has been recognized as a cellular target molecule of CN; if the CN activity is absent, said molecule cannot be dephosphorylated for action in the cell nucleus, so the active transcription complex on the IL-2 promoter cannot be switched on (M. K. Rosen, S. L. Schreiber, *Angew. Chem.* 104 (1992), 413–430; G. Fischer, *Angew. Chem.* 106 (1994), 1479–1501).

Allergic asthmatic diseases arise from an inflammatory reaction controlled by T cells and their mediators. Corticosteroids are still the preferred drugs in the treatment of many allergic diseases. CsA and FK 506 have also proved to be favourable therapeutic agents for bronchial asthma and underlying inflammations, in both animal experiments and clinical studies. In animal experiments it has been possible to demonstrate the blocking of various cytokines, like IL-2, IL-4 and IL-5, which cause allergy-induced inflammations.

Despite the numerous attempts to identify new active immunophilin inhibitors, it has hitherto been impossible to prepare or isolate more active structures than CsA, FK 506, rapamycin or derivatives of these natural substances. However, the high inhibitory potential of CsA, FK 506 and rapamycin is very considerably reduced by the manifold side effects, especially on the kidneys, and neurotoxicity (N. H. Sigal et al., *J. Exp. Med.* 173, 619–628, 1991). The background to this fact is the non-specificity of the interaction between immunophilin ligands and the cell-specific binding proteins. It is this which substantially restricts the known medicinal-therapeutic action of these immunosuppressants. The absence of selectivity of the compounds proves to be a further problem, especially in long-term therapy.

SUMMARY OF THE INVENTION

The object of the invention is to find novel compounds with valuable pharmacological properties and to prepare them by specific synthesis.

The compounds of the formula I according to the invention represent a completely novel class of substances which surprisingly bind immunophilins specifically and surprisingly inhibit IL-2 proliferation. This class of compounds and their pharmaceutically acceptable salts exhibit a high affinity for immunophilins such as CypA, CypB, CypC and FKBP12.

The compounds of the formula I which contain asymmetric carbon atoms, and are therefore normally obtained as racemates, can be resolved into the optically active isomers in a manner known per se, for example with an optically active acid. However, it is also possible to use optically active starting substances at the outset, in which case corresponding optically active or diastereoisomeric compounds are obtained as the end products.

Thus the invention includes the R form, the S form and R,S mixtures of compounds of the formula I which contain one asymmetric carbon atom, and the diastereoisomeric forms as well in the case of several asymmetric carbon atoms.

Depending on the process conditions and starting materials, the compounds of the formula I can be obtained as free compounds or in the form of their salts. The salts obtained can be converted to the free bases or acids in a manner known per se, for example with acids, alkali or ion exchangers.

The compounds of the formula I freed in this way can be converted to the appropriate biocompatible acid addition salts with inorganic or organic acids or bases.

Both the free bases and their salts are biologically active. The compounds of the formula I can be administered in the free form or as salts with a biocompatible acid or base. They can be administered orally, parenterally, intravenously, transdermally or by inhalation.

The invention further relates to pharmaceutical formulations containing at least one compound of the formula I or their salts with biocompatible inorganic or organic acids or bases, and optionally pharmaceutically acceptable excipients and adjuncts.

Examples of suitable forms of administration are tablets or coated tablets, capsules, solutions or ampoules, suppositories, plasters or powder formulations for use in inhalers.

The dosage of the abovementioned pharmaceutical formulations depends on the patient's condition and the form of administration. The daily dose of active substance is between 0.01 and 100 mg per kg of body weight per day.

The compounds represented by the formula I are prepared for example by R. B. Merrifield's solid phase synthesis, preferably on an insoluble polymer such as polystyrene resin in bead form which is swellable in organic solvents (for example a copolymer of polystyrene and 1% of divinylbenzene), using standard peptide coupling methods of solid phase peptide synthesis.

The compounds of the general formula I are prepared by a process in which firstly two of the functional groups (α-amino or ε-amino group and α-carboxylic acid group) are provided with protecting groups and then the free third functional group is reacted in appropriate manner. Another option, where this leads to better results, is to introduce intermediate protecting groups in the first step and exchange them for the desired functional group after the second step. Suitable protecting groups and processes for their introduction are known in the art. Examples of protecting groups are described in "Principles of Peptide Synthesis", Springer Verlag 1984), in the textbook "Solid Phase Peptide Synthesis", J. M. Stewart and J. D. Young, Pierce Chem. Company, Rockford, Ill., 1984, and in G. Barany and R. B. Merrifield, "The Peptides", Ch. 1, pp. 1–285, 1979, Academic Press Inc.

The stepwise synthesis is carried out for example by a process in which firstly the carboxy-terminal amino acid, whose α-amino group is protected, is covalently bonded to an insoluble carrier conventionally used for this purpose, the α-amino protecting group of this amino acid is cleaved, the next protected amino acid is bonded via its carboxyl group to the amino group which has now been freed, the remaining amino acids of the peptide to be synthesized are coupled stepwise in this way in the correct order, any other side-group protecting groups present are cleaved and, when all the amino acids have been coupled, the finished ligand as an immobilized compound is tested for Cyp or FKBP binding. The stepwise condensation is effected in conventional manner by synthesis from the appropriate, conventionally protected amino acids. It is also possible to use automatic peptide synthesizers, for example of the Labortec SP 650 type from Bachem, Switzerland, with the commercially available protected amino acids.

The following may be mentioned as Examples of compounds of the formula I:

Example 1 N-[1-Boc-piperidyl-4-carbonyl]indoline-2-(R,S)-carboxylic acid [S-(N-ε-Boc)lysine methyl ester] amide Example 2 N-[piperidyl-4-carbonyl]indoline-2-(R,S)-carboxylic acid [S-(ε-NH$_2$)lysine methyl ester]amide Example 3 N-[1-Boc-indoline-2-(R,S)-carbonyl]indoline-2-(R,S)-carboxylic acid [S-(N-ε-Boc)lysine methyl ester] amide Example 4 N-[indoline-2-(R,S)-carbonyl]indoline-2-(R,S)-carboxylic acid [S-(ε-NH$_2$)lysine methyl ester]amide Example 5 N-[1-Boc-indoline-2-(R,S)-carbonyl]indoline-2-(R,S)-carboxylic acid [S-(N-ε-Z)lysine methyl ester] amide Example 6 1-Boc-indoline-2-(R,S)-carboxylic acid [S-(N-ε-Z)lysine methyl ester]amide Example 7 1-Boc-indoline-2-(R,S)-carboxylic acid (S-phenylalanine methyl ester)amide Example 8 N-[N'-(4-methoxyphenylacetyl)piperidyl-4-carbonyl]indoline-2-(R,S)-carboxylic acid methyl ester (as a precursor for the preparation of an amide of the general formula I)

Example 9 N-(4-methoxyphenylacetyl)indoline-2-(R,S)-carboxylic acid methyl ester (as a precursor for the preparation of an amide of the general formula I)

Example 10 N-Boc-indoline-2-(R,S)-carboxylic acid 4-piperidylamide

Example 11 N-Boc-indoline-2-(R,S)-carboxylic acid (piperazinoacetic acid morpholide)amide Example 12 N-[1-Boc-piperidyl-4-carbonyl]indoline-2-(R,S)-carboxylic acid (piperazinoacetic acid morpholide) amide Example 13 N-[N'-(4-methoxyphenylacetyl)piperidyl-4-carbonyl]indoline-2-(R,S)-carboxylic acid [S-(N-ε-Z)lysine methyl ester]amide According to the present invention the compounds of the formula I can also be prepared by the following process:

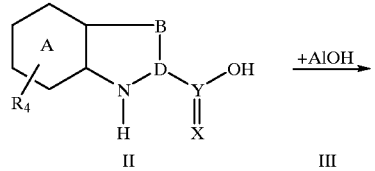

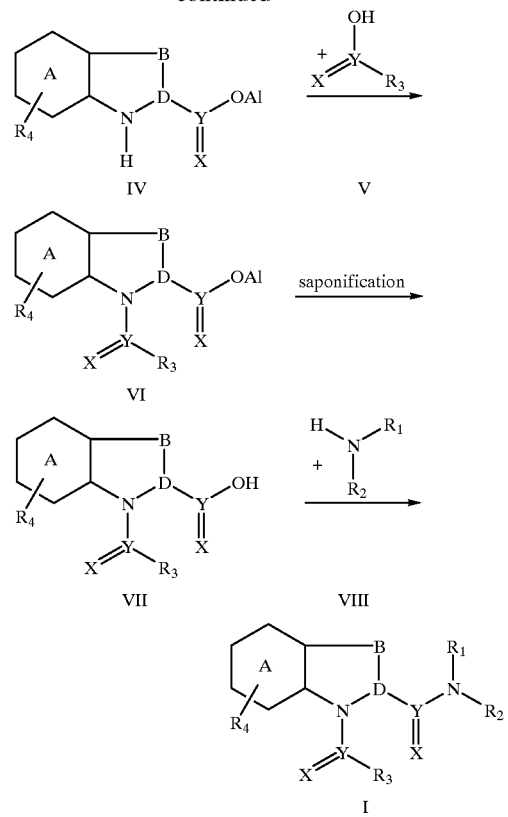

According to the invention, compounds of the formula I, in which R$_1$, R$_2$, R$_3$, R$_4$, A, B, D, X and Y are as defined, are prepared by reacting an indole derivative of the formula II, in which R$_4$, A, B, D, X and Y are as defined, with an alkanol III of C$_1$–C$_{12}$ chain length to give an indole derivative alkyl ester IV, in which R$_4$, A, B, D, X and Y are as defined, subsequently reacting this ester IV with a compound V, in which R$_3$, X and Y are as defined, to give a compound VI, in which R$_3$, R$_4$, A, B, D, X and Y are as defined, then saponifying this compound VI to give a compound VII, in which R$_3$, R$_4$, A, B, D, X and Y are as defined, and then reacting the compound VII with a compound VIII, in which R$_1$ and R$_2$ are as defined, to give the target compound I.

For preparation of the biocompatible salts, the compounds of the formula I are reacted in known manner with inorganic or organic acids, e.g. hydrochloric acid, hydrobromic acid, phosphoric acid, sulphuric acid, acetic acid, tartaric acid, citric acid, fumaric acid, maleic acid, lactic acid or embonic acid, or with inorganic or organic bases.

Pharmaceutical formulations contain at least one compound of the general formula I or their salts with biocompatible inorganic or organic acids or bases, and optionally pharmaceutically acceptable excipients and adjuncts.

The compounds of the formula I can be administered orally, parenterally, intravenously, transdermally or by inhalation, in the free form or as salts with a biocompatible acid or base.

Examples of forms of administration are tablets or coated tablets, capsules, solutions or ampoules, suppositories, plasters or powder formulations for use in inhalers.

The dosage of these abovementioned pharmaceutical formulations depends on the patient's condition and the form of administration. The daily dose of active substance is between 0.01 and 100 mg per kg of body weight.

The compounds of the formula (I) according to the invention are distinguished by binding to immunophilins and inhibit their isomerase activity. This prolyl isomerase activity is assayed by an enzyme test conventionally used throughout the world: G. Fischer, H. Bang, A. Schellenberger, *Biochim. Biophys. Acta,* 791, 87–97, 1984; D. H. Rich et al., *J. Med. Chem.* 38, 4164–4170, 1995.

Although the peptidyl cis/trans-isomerase activity of immunophilins is not affected in every case, such compounds inhibit IL-2 proliferation from mast cells, macrophages and activated T cells with surprising specificity. Like cyclosporin A (Sandimmun®, CsA), FK 506 or rapamycin (Tacrolimus), the compounds according to the invention can be used as immunosuppressants (R. Y. Calne et al., *Br. Med. J.* 282, 934–936, 1981), for the treatment of autoimmune diseases (R. H. Wiener et al., *Hepatology* 7, 1025, Abst. 9, 1987; L. Fry, *J. Autoimmun.* 5, 231–240, 1992; G. J. Feutren, *J. Autoimmun.* 5, 183–195, 1992; EP 610,743), allergic inflammations (P. Zabel et al., *Lancet* 343, 1984), Asthma (C. Bachert, Atemw.- Lungenkrkh. 20, 59, 2994), insulin-dependent diabetes mellitus (C. R. Stiller, *Science,* 223, 1362–1367, 1984) and sepsis, and also in combination with known immunophilin ligands like CsA, FK 506 or rapamycin (M. J. Wyvratt, N. H. Sigal, *Perspectives in Drug Discovery and Design,* Immunosuppression, 2, 1, 1994; WO 92/21313; U.S. Pat. No. 5,330,993).

DETAILED DESCRIPTION OF THE INVENTION

The invention is illustrated in greater detail below by means of Examples, in which the following abbreviations are used:

| | |
|---|---|
| AcOEt | ethyl acetate |
| Boc | tert-butoxycarbonyl |
| (Boc)$_2$O | tert-butoxycarbonyl anhydride |
| CN | calcineurin |
| CsA | cyclosporin A |
| Cyp | cyclophilin |
| DMAP | N,N-dimethylaminopyridine |
| EA | elemental analysis |
| FKBP | FK 506 binding protein |
| HPLC | high pressure liquid chromatography |
| MeOH | methanol |
| PPlase | peptidyl-proline cis/trans-isomerase |
| RT | room temperature |
| TFA | trifluoroacetic acid |
| Z | benzyloxycarbonyl |

EXAMPLE 1

Synthesis of: N-[1-Boc-piperidyl-4-carbonyl]indoline-2-(R,S)-carboxylic acid [S-(N-ε-Boc)-lysine methyl ester]amide Step 1: (R,S)-indoline-2-carboxylic acid methyl ester×HCl In a 100 ml three-necked flask, 5.3 g (32.5 mmol) of (R,S)-indoline-2-carboxylic acid were dissolved in 70 ml of anhydrous methanol, and 4.25 g (35.75 mmol) of thionyl chloride were added at room temperature. The yellow reaction mixture was refluxed for 5 h and, after cooling, the solvent was removed under vacuum on a rotary evaporator. After drying under an oil pump vacuum, the crude product was obtained in the form of a crystalline solid, which was stirred with diethyl ether and filtered off with suction.

Yield: 5.4 g (78%)

Step 2: Boc-piperidine-4-carboxylic acid

In a 250 ml one-necked flask, 7 g (54 mmol) of piperidine-4-carboxylic acid were dissolved in 50 ml of dioxane and 40.5 ml of 2 N NaOH and the solution was cooled to 0° C. A solution of 12.99 g (59.4 mmol) of (Boc)$_2$O in 30 ml of dioxane was added dropwise over 30 min. The mixture was then stirred for 24 h at room temperature. A white precipitate was formed. The dioxane was removed under vacuum on a rotary evaporator and the residue was taken up with saturated KHSO$_4$ solution. The aqueous phase was extracted twice with AcOEt. The organic phase was washed once with saturated NaCl solution and dried over MgSO$_4$. After removal of the solvent under vacuum on a rotary evaporator, 11.93 g (96%) of a white powder were obtained.

$^1$H NMR (DMSO-d$^6$, 270 MHz): 1.25–1.5 (m, 11, Boc, 2-pip); 1.8 (m, 2-pip); 2.4 (m, 1, H—C4); 2.8 (t, 2, H—C3, H—C5); 3.8 (d, 2, H—C2, H—C6); 12.25 (s, 1, COOH).

EA: calculated for C$_{11}$H$_{19}$N$_1$O$_4$ (229.1): C 57.62; H 8.29; N 6.11. found: C 57.89; H 8.36; N 5.86.

Step 3: N-[1-Boc-piperidyl-4-carbonyl]indoline-2-(R,S)-carboxylic acid methyl ester 4.6 g (22 mmol) of (R,S)-indoline-2-carboxylic acid methyl ester×HCl and 7.4 g (32 mmol) of Boc-piperidine-4-carboxylic acid were dissolved in 50 ml of CH$_2$Cl$_2$ and the solution was added dropwise over 30 min at room temperature to a suspension of 9.27 g (36 mmol) of 2-chloro-1-methylpyridinium iodide and 8.06 ml (58 mmol) of triethylamine in 40 ml of CH$_2$Cl$_2$. The mixture was then refluxed for 8 h. The solvent was removed under vacuum on a rotary evaporator, the residue was taken up with 200 ml of AcOEt and the organic phase was washed once with water, twice with semisaturated aqueous KHSO$_4$ solution, twice with 2 N aqueous NaOH solution and once with saturated aqueous NaCl solution. The solvent was removed under vacuum on a rotary evaporator and the residue was purified by chromatography on 400 g of silica gel with CH$_2$Cl$_2$/MeOH 95:5. After removal of the solvent under vacuum on a rotary evaporator and drying under an oil pump vacuum, 4.61 g (54%) of a light brown powder were obtained.

M.p.: 54–56°

TLC: CH$_2$Cl$_2$/MeOH 95:5; R$_f$=0.61

$^1$H NMR (DMSO-d$^6$, 270 MHz): 1.35–1.85 (m, 15, Boc, 6-pip); 2.7–2.8 (m, 2, H—C3, H—C5); 3.25 (m, 1, H—C3-ind); 3.65 (m, 1, H—C3'-ind); 3.8 (s, 3, COOCH$_3$); 3.95 (m, 2, H—C6-pip); 5.45 (d, 1, H—C2-ind); 7.05 (m, 1, Ar); 7.1–7.3 (m, 2, Ar); 8.1 (d, 1, Ar).

EA: calculated for C$_{21}$H$_{28}$N$_2$O$_5$ (388.47): C 64.92; H 7.27; N 7.21. found: C 65.20; H 7.49; N 7.38

MS: (ESI+): calculated: 388.3; found: 389.2.

Step 4: N-[1-Boc-piperidyl-4-carbonyl]indoline-2-(R,S)-carboxylic acid

In a 50 ml one-necked flask, 3.3 g (8.51 mmol) of N-[1-Boc-piperidyl-4-carbonyl]indoline-2-(R,S)-carboxylic acid methyl ester were dissolved in 25 ml of MeOH, 2.14 g (51 mmol) of LiOH×H$_2$O were added and the mixture was stirred for 2.5 h at room temperature. The solution was acidified to pH 5 with semisaturated aqueous KHSO$_4$ solution and extracted twice with AcOEt. The organic phase was washed once with saturated NaCl solution and dried over MgSO$_4$ and the solvent was removed under vacuum on a rotary evaporator. After drying under an oil pump vacuum, 3.09 g (97%) of a light brown powder were obtained.

M.p.: 118–119°

TLC: CH$_2$Cl$_2$/MeOH 95:5; R$_f$=0.14

$^1$H NMR (DMSO-d$^6$, 270 MHz): 1.35–1.85 (m, 15, Boc, 6-pip); 2.7–2.85 (m, 2, H—C3, H—C5); 3.2 (m, 1, H—C3-ind); 3.65 (m, 1, H—C3'-ind); 3.95 (m, 2, H—C6-pip); 5.45 (d, 1, H—C2-ind); 7.05 (m, 1, Ar); 7.1–7.3 (m, 2, Ar); 8.1 (d, 1, Ar); 13.0–13.3 (s, 1, COOH).

MS: (ESI+): calculated: 374.3; found: 375.1.

Step 5: N-[1-Boc-piperidyl-4-carbonyl]indoline-2-(R,S)-carboxylic acid [S-(N-ε-Boc)lysine methyl ester]amide 2 g (5.35 mmol) of N-[1-Boc-piperidyl-4-carbonyl] indoline-2-(R,S)-carboxylic acid and 1.59 g (5.35 mmol) of N-ε-Boc-lysine methyl ester×HCl were dissolved in 20 ml of $CH_2Cl_2$ and the solution was added dropwise over 30 min at room temperature to a suspension of 2.81 g (11 mmol, 2.73 g) of 2-chloro-1-methylpyridinium iodide and 1.62 g (16 mmol) of triethylamine in 30 ml of $CH_2Cl_2$. The mixture was then refluxed for 8 h. The solvent was removed under vacuum on a rotary evaporator, the residue was taken up with 200 ml of AcOEt and the organic phase was washed once with water, twice with semisaturated aqueous $KHSO_4$ solution, twice with 2 N aqueous NaOH solution and once with saturated aqueous NaCl solution The solvent was removed under vacuum on a rotary evaporator and the residue was purified by chromatography on 400 g of silica gel with $CH_2Cl_2$/MeOH 95:5. After removal of the solvent again under vacuum on a rotary evaporator and drying under an oil pump vacuum, 2.61 g (79%) of a light brown powder were obtained.

M.p.: 83–84°

TLC: $CH_2Cl_2$/MeOH 95:5; $R_f$=0.48

FT-IR (KBr): 3365w (N—H); 2976w (C—H); 1744m (C=O); 1684s (CONH); 1540w (C—O); 1407m (C—H); 1170s (C—O); 755m (C=C).

$^1$H NMR (DMSO-$d^6$, 270 MHz): 1.25–1.9 (m, 28, 18 Boc+3 $CH_2$-lys+4-pip); 2.7–3.05 (m, 5, ε-$CH_2$-lys+H—C3-ind+2-pip); 3.55–3.7 (m, 3, COOMe); 3.9–4.1 (m, 2, pip); 4.15–4.3 (m, 1, H—C3-ind); 5.15 (m, 1, H—C2-ind); 6.8 (m, 1, Ar-ind); 7.0 (m, 1, Ar-ind); 7.1–7.3 (m, 2, Ar-ind+α-NHCO); 8.1 (d, 1, Ar-ind); 8.7–8.9 (dd, NHCO-Boc).

MS: (ESI+): calculated: 616.4; found: 617.5

HPLC: 2 peaks at 24.25 and 24.63 min

EA: calculated for $C_{32}H_{48}N_4O_8$ (616.4): C 62.34; H 7.47; N 9.09. found: C 62.08; H 7.67; N 8.86.

EXAMPLE 2

Synthesis of: N-[1-piperidyl-4-carbonyl]indoline-2-(R,S)-carboxylic acid [S-(ε-$NH_2$)lysine methyl ester]amide In a 25 ml one-necked flask, 500 mg (0.812 mmol) of N-[1-Boc-piperidyl-4-carbonyl]indoline-2-(R,S)-carboxylic acid [S-(N-ε-Boc)lysine methyl ester]amide were dissolved in 2.8 ml of $CH_2Cl_2$. 15 eq (0.0122 mol, 0.93 ml) of trifluoroacetic acid were added and the mixture was stirred for two hours at room temperature. 10 ml of diethyl ether were added to the solution and the white precipitate formed was filtered off with suction and washed 6 times with diethyl ether. After drying under an oil pump vacuum, 513 mg (98%) of a white powder were obtained.

M.p.: 164–165°

TLC (RP): $CH_3CN/H_2O$ 1:1, 1% TFA; $R_f$=0.61

FT-IR (KBr): 3435w (N—H); 3049w (C—H); 1740w (C=O); 1676s (CONH); 1420m (C—H); 1205m, 1135s (C—O).

$^1$H NMR (DMSO-$d^6$, 270 MHz): 1.2–2.05 (m, 10, 3 $CH_2$-lys+4-pip); 2.7–3.15 (m, 5, ε-$CH_2$-lys+H—C3-ind+2-pip); 3.55–3.7 (m, 3, COOMe); 4.1–4.25 (m, 1, C3-ind); 5.15 (d, 1, H—C2-ind); 6.95 (m, 1, Ar-ind); 7.1–7.3 (m, 2, Ar-ind); 7.7–7.85 (s, 3, $NH_3$); 8.1 (d, 1, Ar-ind); 8.7–8.9 (m, 2, $NH_2^+$).

MS: (ESI+): calculated: 418.2; found: 417.3 and 209.1 for m/2

HPLC: 2 peaks at 11.54 at 12.65 min

EXAMPLE 3

Synthesis of: N-[1-Boc-indoline-2-(R,S)-carbonyl] indoline-2-(R,S)-carboxylic acid [S-(N-ε-Boc)lysine methyl ester]amide Step 1: Boc-(R,S)-indoline-2-carboxylic acid In a 250 ml one-necked flask, 5 g (30.8 mmol) of (R,S)-indoline-2-carboxylic acid were dissolved in 30 ml of dioxane and 23 ml of 2 N NaOH and the solution was cooled to 0° C. A solution of 7.39 g (33.9 mmol) of $(Boc)_2O$ in 20 ml of dioxane was added dropwise over 30 min and the mixture was stirred for 24 h at room temperature. A white precipitate was formed. The dioxane was removed under vacuum on a rotary evaporator and the residue was taken up with saturated $KHSO_4$ solution and extracted twice with AcOEt. The organic phase was washed once with saturated NaCl solution and dried over $MgSO_4$. After removal of the solvent under vacuum on a rotary evaporator and, drying under an oil pump vacuum, 7.76 g (96%.) of a brown powder were obtained.

TLC: $CH_2Cl_2$/MeOH 95:5+1% $NEt_3$; $R_f$=0.91

$^1$H NMR (DMSO-$d^6$, 270 MHz): 1.4–1.7 (s, 9, Boc); 3.1 (m, 1, H—C3); 3.5 (m, 1, H—C3'); 4.9 (m, 1, H—C2); 7.0 (m, 1, Ar); 7.1–7.3 (m, 2, Ar); 7.5–7.9 (m, 1, Ar); 11.5 (m, 1, COOH).

EA: calculated for $C_{14}H_{17}N_1O_4$ (263.2): C 63.88; H 6.46; N 5.32. found: C 64.05; H 6.53; N 5.41.

Step 2: N-[1-Boc-indoline-2-(R,S)-carbonyl]indoline-2-(R,S)-carboxylic acid methyl ester 5 g (0.023 mol) of (R,S)-indoline-2-carboxylic acid methyl ester×HCl and 12.11 g (46 mmol) of Boc-indoline-2-(R,S)-carboxylic acid were dissolved in 40 ml of $CH_2Cl_2$ and the solution was added dropwise over 30 min at room temperature to a suspension of 12.92 g (51 mmol) of 2-chloro-1-methylpyridinium iodide and 10.23 ml (74 mmol) of triethylamine in 40 ml of $CH_2Cl_2$. The mixture was then refluxed for 8 h. The solvent was removed under vacuum on a rotary evaporator, the residue was taken up with 200 ml of AcOEt and the organic phase was washed once with water, twice with semisaturated aqueous $KHSO_4$ solution, twice with 2 N aqueous NaOH solution and once with saturated aqueous NaCl solution. The solvent was removed under vacuum on a rotary evaporator and the residue was purified by chromatography on 400 g of silica gel with $CH_2Cl_2$/MeOH 95:5. After removal of the solvent under vacuum on a rotary evaporator and drying under an oil pump vacuum, 5.01 g (51%) of a dark brown powder were obtained.

M.p.: 86° C.

TLC: $CH_2Cl_2$/MeOH 95:5; $R_f$=0.67 and 0.7

FT-IR (KBr): 3448w (N—H); 2976w (C—H); 1751s, 1707s (C=O); 1680s (CONH); 1485s (C—H); 1168m (C—O); 1020m (C—O); 752s (C=C).

MS: (ESI+): calculated: 422.4; found: 423.3

EA: calculated for $C_{24}H_{26}N_2O_5$ (422.4): C 68.25; H 6.16; N 6.64. found: C 67.96; H 6.17; N 6.4.

Step 3: N-[1-Boc-indoline-2-(R,S)-carbonyl]indoline-2-(R,S)-carboxylic acid

In a 50 ml one-necked flask, 2.84 g (6.77 mmol) of N-[1-Boc-indoline-2-(R,S)-carbonyl]indoline-2-(R,S)-carboxylic acid methyl ester were dissolved in 20 ml of MeOH. 1.71 g (41 mmol) of LiOH×$H_2O$ were added and the mixture was stirred for 2.5 h at room temperature. The solution was then acidified to pH 5 with semisaturated $KHSO_4$ solution and extracted twice with AcOEt. The organic phase was washed once with saturated NaCl solution and dried over $MgSO_4$ and the solvent was removed under vacuum on a rotary evaporator. After drying under an oil pump vacuum, 2.71 g (98%) of a dark brown powder were obtained.

M.p.: 118–119°

TLC: $CH_2Cl_2$/MeOH 95:5; $R_f$=0.14

MS: (ESI+): calculated: 408.2; found: 409.3.

Step 4: N-[1-Boc-indoline-2-(R,S)-carbonyl]indoline-2-(R,S)-carboxylic acid [S-(N-ε-Boc)lysine methyl ester]amide 2 g (4.9 mmol) of N-[1-Boc-indoline-2-(R,S)-carbonyl]indoline-2-(R,S)-carboxylic acid and 1.45 g (4.9 mmol) of N-ε-Boc-S-lysine methyl ester×HCl were dissolved in 20 ml of $CH_2Cl_2$ and the solution was added dropwise over 30 min at room temperature to a suspension of 2.51 g (9.8 mmol) of 2-chloro-1-methylpyridinium iodide and 2.04 ml (14.7 mmol) of triethylamine in 30 ml of $CH_2Cl_2$. The mixture was then refluxed for 8 h. The solvent was removed under vacuum on a rotary evaporator, the residue was taken up with 200 ml of AcOEt and the organic phase was washed once with water, twice with semisaturated aqueous $KHSO_4$ solution, twice with 2 N aqueous NaOH solution and once with saturated aqueous NaCl solution. The solvent was removed under vacuum on a rotary evaporator and the residue was purified by chromatography on 400 g of silica gel with $CH_2Cl_2$/MeOH 95:5. After removal of the solvent under vacuum on a rotary evaporator and drying under an oil pump vacuum, 2.21 g (69%) of a brown powder were obtained.

M.p.: 78–80°

TLC: $CH_2Cl_2$/MeOH 95:5; $R_f$=0.51

FT-IR (KBr): 3504w (N—H); 2975w (C—H); 1749s, 1690s (CONH, C=O); 1490s (C—H); 1407m (C—H); 1170s (C—O); 757m (C=C).

$^1$H NMR (DMSO-d$^6$, 270 MHz): 1.2–1.8 (m, 24, 18 Boc, 3 $CH_2$-lys); 2.8–3.0 (m, 3, ε-$CH_2$-lys, H—C3-ind); 3.0–3.2 (m, 1, H—C3-ind); 3.4–3.5 (m, 1, H—C3-ind); 3.5–3.7 (m, 3, COOMe); 4.2–4.3 (m, 1, H—C3-ind); 4.7–4.9 (m, 1, H—C2-ind); 5.0–5.5 (m, 1, H—C2-ind); 6.7–6.8 (m, 1, Ar-ind); 6.85–7.3 (m, 6, Ar-ind); 7.7–8.9 (m, 3, NHCO, Ar-ind, α-NHCO).

MS: (ESI+): calculated: 650.2; found: 651.4

HPLC: 4 peaks at 24.82 min, 29.9 min, 30.3 min and 31.2 min

EXAMPLE 4

Synthesis of: N-[indoline-2-(R,S)-carbonyl]indoline-2-(R,S)-carboxylic acid [S-(ε-$NH_2$)lysine methyl ester]amide In a 25 ml one-necked flask, 500 mg (0.812 mmol) of N-[1-Boc-indoline-2-(R,S)-carbonyl]indoline-2-(R,S)-carboxylic acid [S-(N-ε-Boc)lysine methyl ester]amide were dissolved in 2.8 ml of $CH_2Cl_2$. 15 eq (0.0122 mol, 0.93 ml) of trifluoroacetic acid were added and the mixture was stirred for two hours at room temperature. 10 ml of diethyl ether were added to the solution and the white precipitate formed was filtered off with suction and washed 6 times with diethyl ether. After drying under an oil pump vacuum, 513 mg (98%) of a white powder were obtained.

M.p.: 164–165°

TLC (RP): $CH_3CN$/$H_2O$ 1:1, 1% TFA; $R_f$=0.61

FT-IR (KBr): 3435w (N—H); 3049w (C—H); 1740w (C=O); 1676s (CONH); 1420m (C—H); 1205m, 1135s (C—O).

$^1$H NMR (DMSO-d$^6$, 270 MHz): 1.2–2.05 (m, 10, 3 $CH_2$-lys+4-pip); 2.7–3.15 (m, 5, ε-$CH_2$-lys+H—C3-ind+2-pip); 3.55–3.7 (m, 3, COOMe); 4.1–4.25 (m, 1, C3-ind); 5.15 (d, 1, H—C2-ind); 6.95 (m, 1, Ar-ind); 7.1–7.3 (m, 2, Ar-ind); 7.7–7.85 (s, 3, $NH_3^+$); 8.1 (d, 1, Ar-ind); 8.7–8.9 (m, 2, $NH_2^+$).

MS.: (ESI+): calculated: 418.2; found 417.3 and 209.1 for m/2

HPLC: 2 peaks at 11.54 and 12.65 min

EXAMPLE 5

Synthesis of: N-[1-Boc-indoline-2-(R,S)-carbonyl]indoline-2-(R,S)-carboxylic acid [S-(N-ε-Z)lysine methyl ester]amide 2.5 g (6.13 mmol) of N-[1-Boc-indoline-2-(R,S)-carbonyl]indoline-2-(R,S)-carboxylic acid and 2.03 g (6.13 mmol) of N-ε-Z-lysine methyl ester×HCl were dissolved in 20 ml of $CH_2Cl_2$ and the solution was added dropwise over 30 min at room temperature to a suspension of 2.35 g (9.2 mmol) of 2-chloro-1-methylpyridinium iodide and 2.13 ml (15 mmol) of triethylamine in 30 ml of $CH_2Cl_2$. The mixture was then refluxed for 8 h. The solvent was removed under vacuum on a rotary evaporator, the residue was taken up with 200 ml of AcOEt and the organic phase was washed once with water, twice with semisaturated $KHSO_4$ solution, twice with 2 N NaOH solution and once with saturated NaCl solution. The solvent was removed under vacuum on a rotary evaporator and the residue was purified by chromatography on 400 g of silica gel with $CH_2Cl_2$/MeOH 95:5. After removal of the solvent under vacuum on a rotary evaporator and drying under an oil pump vacuum, 2.57 g (61%) of a brown powder were obtained.

M.p.: 68°

TLC: $CH_2Cl_2$/MeOH 95:5; $R_f$=0.48

FT-IR (KBr): 3329w (N—H); 2935w (C—H); 1701s (C=O); 1485s (C—H); 1260m (C—O); 1149m, 1020m (C—O); 753m (C=C).

MS: (ESI+): calculated: 684.5; found: 685.4

EA: calculated for $C_{38}H_{44}N_4O_8$ (684.5): C 66.67; H 6.43; N 8.19. found: C 64.15; H 6.5; N 7.88.

EXAMPLE 6

Synthesis of: 1-Boc-indoline-2-(R,S)-carboxylic acid [S-(N-ε-Z)lysine methyl ester]amide 6.36 g (0.0242 mol) of 1-Boc-indoline-2-(R,S)-carboxylic acid and 8.0 g (24.2 mmol) of N-ε-Z-lysine methyl ester×HCl were dissolved in 70 ml of $CH_2Cl_2$ and the solution was added dropwise over 30 min at room temperature to a suspension of 9.27 g (36.3 mmol) of 2-chloro-1-methylpyridinium iodide and 8.41 ml (60.4 mmol) of triethylamine in 60 ml of $CH_2Cl_2$. The mixture was then refluxed for 8 h. The solvent was removed under vacuum on a rotary evaporator, the residue was taken up with 200 ml of AcOEt and the organic phase was washed once with water, twice with semisaturated $KHSO_4$ solution, twice with 2 N NaOH solution and once with saturated NaCl solution. The solvent was removed under vacuum on a rotary evaporator and the residue was purified by chromatography on 400 g of silica gel with $CH_2Cl_2$/MeOH 95:5. After removal of the solvent under vacuum on a rotary evaporator and drying under an oil pump vacuum, 10.91 g (84%) of a light brown powder were obtained.

TLC: $CH_2Cl_2$/MeOH 95:5; $R_f$=0.74

$^1$H NMR (DMSO-d$^6$, 270 MHz): 1.3–1.75 (m, 15, 9 Boc+6 $CH_2$-lys); 2.8–3.0 (m, 3, $CH_2$-lys+H—C3-ind); 3.4–3.55 (m, 1, H—C3'-ind); 3.65 (s, 3, $COOCH_3$); 4.2 (m, 1, Hα-C-lys); 4.8 (m, 1, H—C2-ind); 5.0 (s, 2, $CH_2$-Z); 6.85 (m, 1, Ar-ind); 7.15 (t, 2, Ar-ind); 7.2–7.4 (m, 5, Ph-Z); 7.7 (m, 1, NHCO); 8.4 (m, 1, Ar-ind).

EA: calculated for $C_{29}H_{37}N_3O_7$ (539.4): C 64.56; H 6.86; N 7.79. found: C 64.61; H 7.06; N 7.67.

MS: (ESI+): calculated: 539.4; found: 540.3.

EXAMPLE 7

Synthesis of: 1-Boc-indoline-2-(R,S)-carboxylic acid (S-phenylalanine methyl ester)amide Step 1: S-phenylalanine methyl ester×HCl In a 100 ml one-necked flask, 5.3 ml (72.6 mmol) of thionyl chloride were added dropwise over 30 min at room temperature to a suspension of 8.0 g (48.4 mmol) of S-phenylalanine in 50 ml of MeOH. The mixture was then refluxed for 3 h. The methanol and excess thionyl chloride were distilled off, firstly under a water jet vacuum and then on a rotary evaporator. The residue was dissolved in 50 ml of MeOH and 800 ml of diethyl ether were added. A white precipitate was formed. The solvent was filtered off with suction through a frit to give 7.93 g (75%) of a white powder.

$^1$H NMR (DMSO-d$^6$, 270 MHz): 3.0–3.2 (m, 2, $CH_2$); 3.65 (s, 3, COOMe); 4.35 (m, 1, Hα-C); 7.2–7.4 (m, 5, Ph); 8.5–8.7 (m, 3, $NH_3^+$).

Step 2: N-[1-Boc-indoline-2-(R,S)-carbonyl]-(S-phenylalanine methyl ester)amide 3.5 g (16.2 mmol) of S-phenylalanine methyl ester hydrochloride and 4.27 g (16.2 mmol) of 1-Boc-indoline-2-(R,S)-carboxylic acid were dissolved in 70 ml of $CH_2Cl_2$ and the solution was added dropwise over 30 min at room temperature to a suspension of 6.21 g (24.3 mmol) of 2-chloro-1-methylpyridinium iodide and 5.32 ml (40.5 mmol) of triethylamine in 60 ml of $CH_2Cl_2$. The reaction mixture was then refluxed for 8 h. The solvent was removed under vacuum on a rotary evaporator, the residue was taken up with 200 ml of AcOEt and the organic phase was washed once with water, twice with semisaturated $KHSO_4$ solution, twice with 2 N NaOH solution and once with saturated NaCl solution. The solvent was removed under vacuum on a rotary evaporator and the residue was purified by chromatography on 400 g of silica gel with $CH_2Cl_2$/MeOH 95:5. After removal of the solvent again under vacuum on a rotary evaporator and drying under an oil pump vacuum, 7.71 g (62%) of a light yellow powder were obtained.

TLC: $CH_2Cl_2$/MeOH 95:5; $R_f$=0.87

$^1$H NMR (DMSO-d$^6$, 270 MHz): 1.2–1.5 (m, 9, Boc); 2.3–2.45 (m, 0.5, H—C3-ind); 2.8–3.5 (m, 3.5, C3-ind+ $CH_2$); 3.65 (d, 3, COOMe); 4.4–4.65 (m, 1, C2-ind); 4.8 (m, 1, Hα-C); 6.8–7.3 (m, 8, 5 Ph+3 Ar-ind); 7.7 (m, 1, Ar-ind); 8.55 (m, 1, NH).

EA: calculated for $C_{24}H_{28}N_2O_5$ (424.3): C 67.92; H 6.6; N 6.6. found: C 67.94; H 6.79; N 6.59.

MS: (ESI+): calculated: 424.4; found: 425.2.

EXAMPLE 8

Synthesis of: N-[N'-(4-methoxyphenylacetyl) piperidyl-4-carbonyl]indoline-2-(R,S)-carboxylic acid methyl ester (This compound can be used as a precursor for the preparation of an amide of the general formula I)

1.2 g (3.0 mmol) of N-[1-Boc-piperidyl-4-carbonyl] indoline-2-(R,S)-carboxylic acid methyl ester were dissolved in 30 ml of $CH_2Cl_2$ at RT, 1.14 g (10 mmol) of TFA were added and the reaction mixture was stirred for 24 h. It was concentrated under vacuum on a rotary evaporator, taken up with 100 ml of ethyl acetate and washed 3 times with saturated aqueous $NaHCO_3$ solution and once with saturated aqueous NaCl solution. The organic phase was dried over $MgSO_4$ and the solvent was removed under vacuum on a rotary evaporator. The residue was dissolved in 30 ml of $CH_2Cl_2$, 1.01 g (10 mmol) of triethylamine and 366 mg (3.0 mmol) of 4-dimethylaminopyridine were added, the mixture was cooled to 0° C. and a solution of 606 mg (3.3 mmol) of 4-methoxyphenylacetyl chloride in 10 ml of $CH_2Cl_2$ was added. After stirring for 24 h, the solvent was removed from the reaction mixture under vacuum on a rotary evaporator and the residue was taken up with 100 ml of ethyl acetate and washed twice with 1 N HCl solution, twice with saturated aqueous $NaHCO_3$ solution and once with saturated aqueous NaCl solution. After distillation of the solvent under vacuum on a rotary evaporator, the residue was chromatographed on 80 g of flash gel with n-hexane/ AcOEt. The appropriate fractions were collected, the solvent was removed under vacuum on a rotary evaporator and the residue was dried under an oil pump vacuum to give 1.1 g of product in the form of a white foam.

TLC: AcOEt; $R_f$=0.22

$^1$H NMR (DMSO-d$^6$, 270 MHz): 1.35–1.85 (m, 13, Boc, 4-pip); 2.7–2.8 (m, 4, H—C(3), H—C(5)); 3.25 (m, 1, H—C(3)-ind); 3.65 (m, 1, H—C(3')-ind); 3.8 (s, 3, $COOCH_3$); 3.95 (m, 1, H—C(4)-pip); 5.45 (d, 1, H—C(2)-ind); 7.05 (m, 1, Ar); 7.1–7.3 (m, 2, Ar); 8.1 (d, 1, Ar).

EA: calculated for $C_{25}H_{28}N_2O_5$ (436.51): C 68.70; H 6.47; N 6.42. found: C 69.97; H 6.98; N 5.27.

EXAMPLE 9

Synthesis of: N-(4-methoxyphenylacetyl)indoline-2-(R,S)-carboxylic acid methyl ester (This compound can be used as a precursor for the preparation of an amide of the general formula I)

1 g of (R,S)-indoline-2-carboxylic acid methyl ester×HCl and 1.14 g (9.36 mmol) of DMAP in 25 ml of dry $CH_2Cl_2$ were placed in a 100 ml one-necked flask with septum. 1.04 g (856 μl) of 4-methoxyphenylacetyl chloride were added dropwise with a syringe over 30 min at 0° C., with stirring. The mixture was then stirred for 3 h at room temperature. The solvent was removed under vacuum on a rotary evaporator and the residue was purified by flash chromatography on 150 g of flash silica gel ($CH_2Cl_2$/MeOH 9:1). After removal of the solvent under vacuum on a rotary evaporator, 830 mg (59%) of a light grey powder were obtained.

TLC: $CH_2Cl_2$; $R_f$=0.31

$^1$H NMR (DMSO-d$^6$, 270 MHz): 3.15–3.3 (m, 1, H—C (3)-ind); 3.5–3.7 (m, 3, $CH_2$+H—C(3')-ind); 5.0 (m, 1, H—C(2)-ind); 6.85 (m, 2, Ar-ind); 7.0 (m, 1, Ar-ind); 7.1–7.3 (m, 4, phenyl); 8.25 (d, 1, Ar-ind).

EA: calculated for $C_{19}H_{19}N_1O_4$ (325.3): C 70.15; H 5.85; N 4.31. found: C 70.34; H 5.78; N 4.22.

MS: (ESI+): calculated: 325.3; found: 326.1.

EXAMPLE 10

Synthesis of: N-Boc-indoline-2-(R,S)-carboxylic acid 4-piperidylamide 2.63 g (10.0 mmol) of 1-Boc-(R,S)-indoline-2-carboxylic acid, 1.13 g (12.0 mmol) of 4-aminopyridine and 1.47 g (12.0 mmol) of 4-dimethylaminopyridine in 30 ml of $CH_2Cl_2$ were placed in a 100 ml one-necked flask at 0° C. and a solution of 2.48 g (12.0 mmol) of dicyclohexylcarbodiimide in 5 ml of $CH_2Cl_2$ was added. After 48 h the reaction mixture was filtered on Celite, the solvent was removed under vacuum on a rotary evaporator and the residue was taken up with 100 ml of ethyl acetate and washed twice with 10% aqueous HCl solution, twice with saturated aqueous NaHCO$_3$ solution and once with saturated aqueous NaCl solution. After distillation of the solvent under vacuum on a rotary evaporator, the residue was chromatographed on 50 g of flash gel with n-hexane/AcOEt. After removal of the solvent under vacuum on a rotary evaporator, the residue was crystallized from AcOEt/ether to give 2.4 g of product.

TLC: CH$_2$Cl$_2$/MeOH=95/5; R$_f$=0.19

$^1$H NMR (CDCl$_3$, 270 MHz): 1.58 (s, 9H, Boc); 3.43–3.54 (m, 2H, H—C(3)-ind); 5.0 (m, 1, H—C2-ind); 7.02 (m, 1H, H—C(7)-ind); 7.17–7.26 (m, 3H, H—C(6), H—C(5), H—C(4)-ind); 7.45 (q, 2H, H—C(3), H—C(5)-py); 7.57 (NH); 8.47 (q, 2H, H—C(2), H—C(6)-py).

EA: calculated for C$_{19}$H$_{21}$N$_3$O$_3$ (339.40): C 67.84; H 6.29; N 12.49. found: C 67.75; H 6.33; N 12.53.

EXAMPLE 11

Synthesis of: N-Boc-indoline-2-(R,S)-carboxylic acid (piperazinoacetic acid morpholide)amide 2.63 g (10.0 mmol) of 1-Boc-(R,S)-indoline-2-carboxylic acid, 2.56 g (12.0 mmol) of piperazinoacetic acid morpholide and 1.47 g (12.0 mmol) of 4-dimethylaminopyridine in 30 ml of CCl$_2$ were placed in a 100 ml one-necked flask at 0° C. and a solution of 2.48 g (12.0 mmol) of dicyclohexylcarbodiimide in 5 ml of CH$_2$Cl$_2$ was added. After 48 h the reaction mixture was filtered on Celite, the solvent was removed under vacuum on a rotary evaporator and the residue was taken up with 100 ml of ethyl acetate and washed twice with 10% aqueous god HCl solution, twice with saturated aqueous NaRCO$_3$ solution and once with saturated aqueous NaCl solution. After distillation of the solvent under vacuum on a rotary evaporator, the residue was chromatographed on 50 g of flash gel with n-hexane/AcOEt. After removal of the solvent under vacuum on a rotary evaporator, the residue was crystallized from AcOEt/ether to give 2.4 g of product.

TLC: CH$_2$Cl$_2$/MeOH 95/5; R$_f$=0.19

$^1$H NMR (CDCl$_3$, 270 MHz): 1.48–1.58 (d, 9H, Boc); 3.21 (s, 2H, H—C(2')); 3.42–3.69 (m, 16H); 5.1 (br, 2H, H—C(3)-ind); 6.48 (g, 1H); 6.90 (q, 1H); 7.14 (m, 1H); 8.22 (q, 1H).

EA: calculated for C$_{24}$H$_{34}$N$_4$O$_5$ (458.56): C 62.86; H 7.47; N 12.21. found: C 63.21; H 7.48; N 13.61.

EXAMPLE 12

Synthesis of: N-[1-Boc-piperidyl-4-carbonyl] indoline-2-(R,S)-carboxylic acid (piperazinoacetic acid morpholide)amide 458.56 mg (1.0 mmol) of 1-Boc-indoline-2-(R,S)-carboxylic acid (piperazinoacetic acid morpholide)amide were dissolved in 20 ml of CH$_2$Cl$_2$ at RT, 1.14 g (10 mmol) of TFA were added and the reaction mixture was stirred for 24 h. It was concentrated under vacuum on a rotary evaporator, taken up with 10 ml of ethyl acetate and washed twice with saturated aqueous NaHCO$_3$ solution and once with saturated aqueous NaCl solution. The organic phase was dried over MgSO$_4$ and the solvent was -removed under vacuum on a rotary evaporator. The residue was dissolved in 10 ml of CH$_2$Cl$_2$, 505 mg (5 mmol) of triethylamine, 320.7 mg (1.4 mmol) of 4-Boc-piperidinecarboxylic acid and 357.7 mg (1.4 mmol) of 2-chloro-1-methylpyridinium hydrochloride were added and the reaction mixture was refluxed for 8 h. The solvent was removed under vacuum on a rotary evaporator and the residue was taken up with 100 ml of ethyl acetate, washed twice with water, once with 10% aqueous HCl solution, twice with saturated aqueous NaHCO$_3$ solution and once with saturated aqueous NaCl solution and dried over MgSO$_4$. After distillation of the solvent under vacuum on a rotary evaporator, the residue was crystallized from ethyl acetate/isopropanol.

EA: calculated for C$_{25}$H$_{28}$N$_2$O$_5$ (557.70): C 62.46; H 7.77; N 12.56. found: C 61.56; H 7.62; N 11.96.

EXAMPLE 13

Synthesis of: N-[N'-(4-methoxyphenylacetyl) piperidyl-4-carbonyl]indoline-2-(R,S)-carboxylic acid [S-(N-ε-Z)lysine methyl ester]amide Step 1: N-[1-Boc-piperidyl-4-carbonyl]indoline-2-(R,S)-carboxylic acid [S-(N-ε-Z)lysine methyl ester]amide 3.74 g (10 mmol) of N-[1-Boc-piperidyl-4-carbonyl]indoline-2-(R,S)-carboxylic acid and 3.31 g (10 mmol) of N-ε-Z-lysine methyl ester×HCl were dissolved in 20 ml of CH$_2$Cl$_2$ and the solution was added dropwise over 30 min at room temperature to a suspension of 5.11 g (20 mmol) of 2-chloro-1-methylpyridinium iodide and 4.04 g (40 mmol) of triethylamine in 30 ml of CH$_2$Cl$_2$. After 8 hours under reflux, the solvent was removed from the reaction mixture under vacuum on a rotary evaporator. The residue was taken up with 200 ml of ethyl acetate and the organic phase was washed once with water, twice with semisaturated aqueous KHSO$_4$ solution, twice with 2 N aqueous NaOH solution and once with saturated aqueous NaCl solution. After drying over MgSO$_4$, the solvent was removed under vacuum on a rotary evaporator and the residue was purified by chromatography on 400 g of silica gel with CH$_2$Cl$_2$/MeOH 95:5. The appropriate fractions were combined and the solvent was removed under vacuum on a rotary evaporator. After drying under an oil pump vacuum, 4.2 g of a light brown powder were obtained.

TLC: CH$_2$Cl$_2$/MeOH 95:5; R$_f$=0.41

EA: calculated for C$_{32}$H$_{48}$N$_4$O$_8$ (650.78): C 64.60; H 7.13; N 8.61. found: C 64.73; H 7.01; N 8.64.

Step 2: N-[N'-(4-methoxyphenylacetyl)piperidyl-4-carbonyl]indoline-2-(R,S)-carboxylic acid [S-(N-ε-Z)lysine methyl ester]amide 3.25 g (5.0 mmol) of N-[1-Boc-piperidyl-4-carbonyl]indoline-2-(R,S)-carboxylic acid [S-(N-ε-Z)lysine methyl ester]amide were dissolved in 50 ml of CH$_2$Cl$_2$ at RT, 2.28 g (20 mmol) of TFA were added and the reaction mixture was stirred for 4 h. It was concentrated under vacuum on a rotary evaporator, taken up with 100 ml of ethyl acetate and washed 3 times with saturated aqueous NaHCO$_3$ solution and once with saturated aqueous NaCl solution. The organic phase was dried over MgSO$_4$ and the solvent was removed under vacuum on a rotary evaporator. The residue was dissolved in 30 ml of CH$_2$Cl$_2$, 1.01 g (10 mmol) of triethylamine and 366 mg (3.0 mmol) of 4-dimethylaminopyridine were added, the mixture was cooled to 0° C. and a solution of 1.01 g (5.5 mmol) of 4-methoxyphenylacetyl chloride in 10 ml of CH$_2$Cl$_2$ was added. After stirring for 24 h, the solvent was removed from the reaction mixture under vacuum on a rotary evaporator and the residue was taken up with 100 ml of ethyl acetate and washed twice with 1 N aqueous HCl solution, twice with saturated aqueous NaHCO$_3$ solution and once with saturated aqueous NaCl solution. After distillation of the solvent under vacuum on a rotary evaporator, the residue was chromatographed on 80 g of flash gel with n-hexane/AcOEt. The appropriate fractions were collected, the solvent was removed under vacuum on a rotary evaporator and the residue was dried under an oil pump vacuum to leave the product in the form of a white foam.

EA: calculated for $C_{39}H_{46}N_4O_8 \times H_2O$ (716.84): C 65.35; H 6.75; N 7.82. found: C 65.47; H 6.89; N 7.81.

Surprisingly, the above Examples 1–7 and 10–13 were found to be strongly binding immunophilin modulators which are suitable as a carrier-fixed form and are capable of binding pathogenically active immunophilins from fluids, especially body fluids.

To find strongly binding CypB or FKBP ligands of the formula I, the immobilized ligands were subjected to SDS-PAGE (FIG. 1) with cell homogenate. Carrier-fixed ligands which have a particular affinity for immunophilins bind them specifically with an affinity which is higher than that of CsA or FK 506. The high affinity for immunophilins of the carrier-fixed ligands represented by the formula I can be demonstrated by SDS-PAGE.

Figure 1:
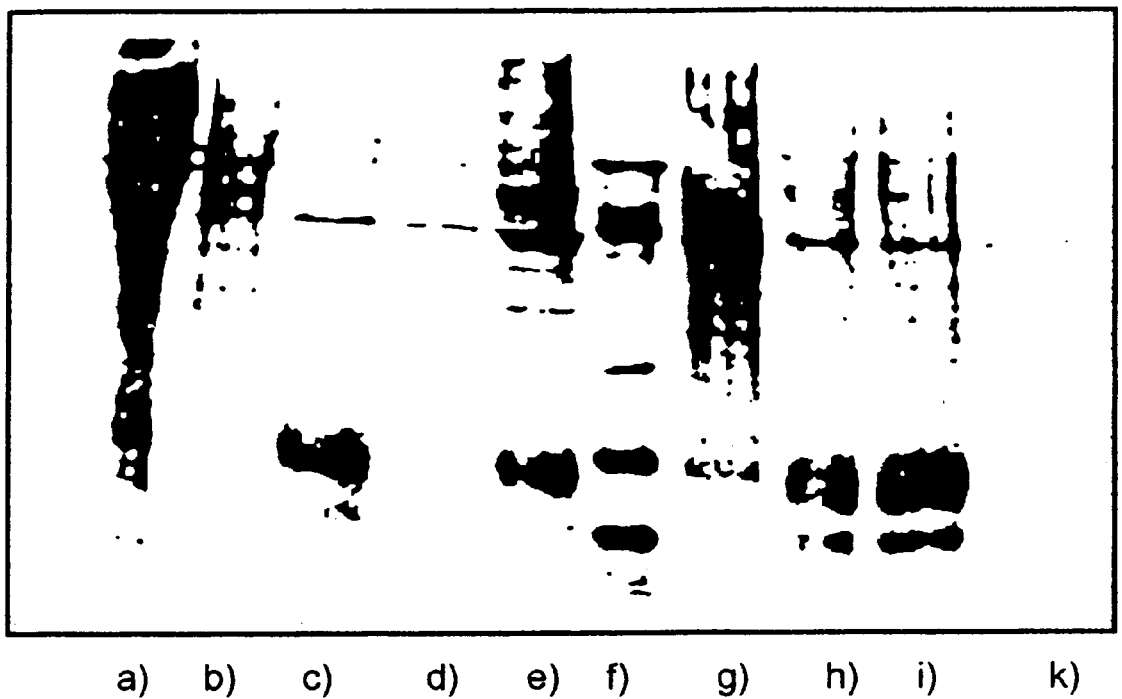
FIG. 1: SDS-PAGE of carrier-fixed ligands with cell homogenate

EXPLANATION OF THE SDS-PAGE a) cell homogenate
b) cell homogenate eluate after equilibration with carrier-fixed ligands of the general formula I
c) separation of the cyclophilin B from the matrix mentioned under b) with SDS at 25° C.
d) SDS control
e) separation of the cyclophilin B from the matrix mentioned under b) with SDS at 95° C.
f) protein standard (Sigma: 12 kDa, 18 kDa, 25 kDa, 45 kDa, 66 kDa)
g) cell homogenate eluate after equilibration with immobilized CsA
h) separation of the cyclophilin B from the CsA matrix mentioned under g) with SDS at 25° C.
i) separation of the cyclophilin B from the CsA matrix mentioned under g) with SDS at 95° C.
k) SDS control Surprisingly, the compounds of the formula (I) according to the invention are distinguished by binding to immunophilins and they inhibit their peptidyl-prolyl cis/trans-isomerase (PPlase) activity. For the initial screening (1 µmol/l substance) the inhibition of human cyclophilin B is determined in the PPlase test. This PPlase activity is assayed by an enzyme test conventionally used throughout the world: G. Fischer, H. Bang, C. Mech, *Biomed. Biochim. Acta*, 43, 1101–1111; G. Fischer, R. Bang, A. Schellenberger, *Biochim. Biophys. Acta*, 791, 87–97, 1984; D. H. Rich et al., *J. Med. Chem.* 38, 4164–4170, 1995.

The compounds of the general formula I according to the invention are preincubated together with 10 nmol of CypB for 15 min at 4° C. The enzyme reaction is started after the addition of chymotrypsin and HEPES buffer with the test peptide Suc-Ala-Ala-Pro-Phe-Nan. The change in extinction at 390 nm is then monitored and evaluated. The change in extinction determined by photometry results from two partial reactions: a) the rapid chymotryptic cleavage of the trans-peptide; and b) the non-enzymatic cis/trans isomerization catalysed by cyclophilins. The corresponding PPlase activity of the compounds of the general formula I according to the invention is shown in Table 1:

TABLE 1

| Compound [10 µmol] | | Inhibition [%] |
|---|---|---|
| Example 1: | N-[1-Boc-piperidyl-4-carbonyl]indoline-2-(R,S)-carboxylic acid [S-(N-ε-Boc)-lysine methyl ester]amide | 0–20 |
| Example 2: | N-[piperidyl-4-carbonyl]indoline-2-(R,S)-carboxylic acid [S-(ε-NH₂)lysine methyl ester]amide | 0–20 |
| Example 3: | N-[1-Boc-inodline-2-(R,S)-carbonyl]indoline-2-(R,S)-carboxylic acid [S-(N-ε-Boc)lysine methyl ester]amide | 0–20 |
| Example 4: | N-[indoline-2-(R,S)-carbonyl]indoline-2-(R,S)-carboxylic acid [S-(ε-NH₂)lysine methyl ester]amide | 0–20 |
| Example 5: | N-[1-Boc-indoline-2-(R,S)-carbonyl]indoline-2-(R,S)-carboxylic acid [S-(N-ε-Z)lysine methyl ester]amide | 0–20 |
| Example 6: | 1-Boc-indoline-2-(R,S)-carboxylic acid [S-(N-ε-Z)lysine methyl ester]amide | 20–40 |
| Example 7: | 1-Boc-indoline-2-(R,S)-carboxylic acid(S-phenylalanine methyl ester)amide | 0–20 |
| Example 8: | N-[N'-(4-methoxyphenyl-acetyl)piperidyl-4-carbonyl]-indoline-2-(R,S)-carboxylic acid methyl ester | 0–20 |
| Example 9: | N-(4-methoxyphenylacetyl)-indoline-2-(R,S)-carboxylic acid methyl ester | 0–20 |
| Example 10: | N-Boc-indoline-2-(R,S)-carboxylic acid 4-piperidylamide | 0–20 |
| Example 11: | N-Boc-indoline-2-(R,S)-carboxylic acid (piperazino-acetic acid morpholide)amide | 0–20 |
| Example 12: | N-[1-Boc-piperidyl-4-carbonyl]indoline-2-(R,S)-carboxylic acid (piperazino-acetic acid morpholide)amide | 0–20 |
| Example 13: | N-[N'-(4-methoxyphenylacetyl)-piperidyl 4-carbonyl]indoline-2-(R,S)-carboxylic acid [S-(N-ε-Z)lysine methyl ester]amide | 0–20 |

The formation of the supermolecule from CsA-CypB-calcineurin ($Ca^{2+}$-dependent phosphatase) seems to be responsible for the known immunosuppressive effects of CsA. To study the interaction with this supermolecule from CsA-CypB or CsA-CypB-calcineurin, the compounds of the general formula I according to the invention were incubated with cell homogenate of a human T cell line containing ³H-CsA (100 nmol). After gel filtration on Superose 12, the radioactivity of the eluted fractions was measured and compared with the untreated control. The corresponding displacement of ³H-CsA from the supermolecules CypB-CsA and CypB-CsA-calcineurin by the compounds of the general formula I according to the invention is shown in Table 2:

TABLE 2

| Compound [10 μmol] | | Displacement from CypB-CsA in [%] | Displacement from CypB-CsA-CN in [%] |
|---|---|---|---|
| Example 1: | N-[1-Boc-piperidyl-4-carbonyl]indoline-2-(R,S)-carboxylic acid [S-(N-ε-Boc)lysine methyl ester]amide | 10 | 45 |
| Example 2: | N-[piperidyl-4-carbonyl]indoline-2-(R,S)-carboxylic acid [S-(ε-NH$_2$)lysine methyl ester]amide | 45 | −53 |
| Example 3: | N-[1-Boc-indoline-2-(R,S)-carbonyl]-indoline-2-(R,S)-carboxylic acid [S-(N-ε-Boc)lysine methyl ester]amide | 14 | 22 |
| Example 4: | N-[indoline-2-(R,S)-carbonyl]indoline-2-(R,S)-carboxylic acid [S-(ε-NH$_2$)lysine methyl ester]amide | 33 | −42 |
| Example 5: | N-[1-Boc-indoline-2-(R,S)-carbonyl]-indoline-2-(R,S)-carboxylic acid [S-(N-ε-Z)lysine methyl ester]amide | 16 | 20 |
| Example 6: | 1-Boc-indoline-2-(R,S)-carboxylic acid [S-(N-ε-Z)lysine methyl ester]amide | 0 | 7 |
| Example 7: | 1-Boc-indoline-2-(R,S)-carboxylic acid (S-phenyl-alanine methyl ester)amide | 38 | 0 |
| Example 8: | N-[N'-(4-methoxyphenyl-acetyl)piperidyl-4-carbonyl]indoline-2-(R,S)-carboxylic acid methyl ester | 0 | 8 |
| Example 9: | N-(4-methoxyphenyl-acetyl)indoline-2-(R,S)-carboxylic acid methyl ester | 39 | 37 |
| Example 10: | N-Boc-indoline-2-(R,S)-carboxylic acid 4-piperidyl-amide | −58 | 0 |
| Example 11: | N-Boc-indoline-2-(R,S)-carboxylic acid (piperazino-acetic acid morpholide)amide | −28 | 0 |
| Example 12: | N-[1-Boc-piperidyl-4-carbonyl]indoline-2-(R,S)-carboxylic acid (piperazinoacetic acid morpholide)amide | 8 | −25 |
| Example 13: | N-[N'-methoxyphenyl-acetyl)piperidyl-4-carbonyl]indoline-2-(R,S)-carboxylic acid [S-(N-ε-Z)lysine methyl ester]amide | 46 | −16 |

The IL-2 proliferation test is based on the incorporation of $^3$H-thymidine into T cells stimulated with OKT-3 (human anti-CD3 antibodies) and is performed as follows:

100,000 T cells are inoculated into 150 μl of culture medium per well in microtitre plates, stimulated by the addition of OKT-3 (1 μg/ml) and incubated for 45 h with each of the compounds of the general formula I according to the invention. After this incubation period, 10 μl of the $^3$H-thymidine solution (0.5 μCi) are pipetted into each well. Incubation is then carried out for 6 h at 37° C. in a 5% CO$_2$ atmosphere. After the cells have been harvested, the radioactivity is quantified in a β-counter. The corresponding CD3-induced inhibition of proliferation by the compounds of the general formula I according to the invention is shown in Table 3:

TABLE 3

| Compound [10 μmol] | | CD3-induced inhibition of proliferation in [%] |
|---|---|---|
| Example 1: | N-[1-Boc-piperidyl-4-carbonyl]indoline-2-(R,S)-carboxylic acid [S-(N-ε-Boc)lysine methyl ester]amide | 86 |
| Example 2: | N-[piperidyl-4-carbonyl]-indoline-2-(R,S)-carboxylic acid [S-(ε-NH$_2$)lysine methylester]-amide | 40 |
| Example 3: | N-[1-Boc-indoline-2-(R,S)-carbonyl]indoline-2-(R,S)-carboylic acid [S-(N-ε-Boc)lysine methyl ester]amide | 82 |
| Example 4: | N-[indoline-2-(R,S)-carbonyl]indoline-2-(R,S)-carboxylic acid [S-(ε-NH$_2$)lysine methyl ester]amide | 38 |
| Example 5: | N-[1-Boc-indoline-2-(R,S)-carbonyl]indoline-2-(R,S)-carboxylic acid [S-(N-ε-Z)lysine methyl ester]amide | 92 |
| Example 6: | 1-Boc-indoline-2-(R,S)-carboxylic acid [S-(N-ε-Z)lysine methyl ester]amide | 84 |
| Example 7: | 1-Boc-indoline-2-(R,S)-carboxylic acid (S-phenylalanine methyl ester)amide | 7 |
| Example 10: | N-Boc-indoline-2-(R,S)-carboxylic acid 4-piperidylamide | 6 |
| Example 11: | N-Boc-indoline-2-(R,S)-carboxylic acid (piperazino-acetic acid morpholide)amide | 9 |
| Example 12: | N-[1-Boc-piperidyl-4-carbonyl]indoline-2-(R,S)-carboxylic acid (piperazinoacetic acid morpholide)amide | 5 |
| Example 13: | N-[N'-(4-methoxyphenyl-acetyl)piperidyl-4-carbonyl]indoline-2-(R,S)-carboxylic acid [S-(N-ε-Z)lysine methyl ester]amide | 66 |

In animal experiments, like CsA, FK 506 or rapamycin, the compounds of the general formula I according to the invention exhibit the blocking of cytokines, like IL-2, IL-4 and IL-5, which cause allergy-induced inflammations in the patient.

To determine the inhibition of cell division by the compounds of the general formula I according to the invention, 50,000 human tumour cells were cultivated for 48 h in the presence of the compounds of the general formula I according to the invention, 10 μl of yellow tetrazolium salt solution (MTT) were added and incubation was carried out for a further 4 h at 37° C. in a CO$_2$ atmosphere. The resulting violet colouration was analysed by photometry at 570 nm. After the addition of 100 μl of SDS solution in each case and incubation overnight, the colouration was quantified by photometry. A general cytotoxicity could not be established for the compounds of the general formula I according to the invention.

What is claimed is:
1. Specific immunophilin ligands of the formula

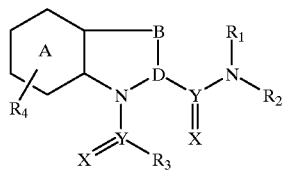

I in which $R_1$, $R_2$, $R_3$, $R_4$, X, Y, A, B and D are defined as follows:

- $R_1$ is hydrogen, a $(C_1-C_{12})$-alkyl group or a $(C_2-C_6)$-alkoxy group, where the alkyl group is linear or branched and is unsubstituted or substituted by a monocyclic or bicyclic heteroaryl having 1–4 heteroatoms, or monosubstituted or polysubstituted by a phenyl ring, said phenyl ring being unsubstituted or monosubstituted or polysubstituted by halogen, $(C_1-C_6)$-alkyl, $(C_3-C_7)$-cycloalkyl, carboxyl groups, carboxyl groups esterified with linear or branched $(C_1-C_6)$-alkanols, carbamoyl groups, tri-fluoromethyl groups, hydroxyl groups, methoxy groups, ethoxy groups, benzyloxy groups or amino groups, which in turn are substituted by benzyl, benzoyl or acetyl; or
- $R_1$ is the amine radical of the methyl esters of the following amino acids: histidine, leucine, valine, serine (Bzl), threonine, pipecolic acid, piperidine-4-carboxylic acid, piperidine-3-carboxylic acid, ε-NH2-lysine, ε-Z-NH-lysine, ε-(2Cl-Z)-NH-lysine, 2-pyridylalanine, phenylalanine, tryptophan, glutamic acid, arginine (Tos), asparagine, citrulline, homocitrulline, ornithine, proline, indoline-2-carboxylic acid, octahydroindolinecarboxylic acid, tetrahydroisoquinolinecarboxylic acid, 5-aminovaleric acid and 8-aminooctanoic acid;
- $R_2$ is hydrogen, a $(C_1-C_{12})$-alkyl group or a $(C_2-C_6)$-alkoxy group, where the alkyl group is linear or branched and is unsubstituted or substituted by a monocyclic or bicyclic heteroaryl having 1–4 heteroatoms, or monosubstituted or polysubstituted by a phenyl ring, said phenyl ring being unsubstiututed or monosubstituted or polysubstituted by halogen, $(C_1-C_6)$-alkyl, $(C_3-C_7)$-cycloalkyl, carboxyl groups, carboxyl groups esterified with linear or branched $(C_1-C_6)$-alkanols, carbamoyl groups, tri-fluoromethyl groups, hydroxyl groups, methoxy groups, ethoxy groups, benzyloxy groups or amino groups, which in turn are substituted by benzyl, benzoyl or acetyl;
- $R_3$ is hydrogen, butoxycarbonyl, carboxybenzyl, mono-, bi-, or tri-cyclic carbonylaryl or carbonylheteroaryl having 1–4 heteroatoms, where said aryl or heteroaryl is unsubstituted, or monosubstituted or polysubstituted by halogen, $(C_1-C_6)$-alkyl, $(C_3-C_7)$-cycloalkyl, carboxyl groups, carboxyl groups esterified with linear or branched $(C_1-C_6)$-alkanols, carbamoyl groups, trifluoromethyl groups, hydroxyl groups, methoxy groups, ethoxy groups, benzyloxy groups or amino groups, which in turn are substituted by benzyl, benzoyl or acetyl; or $R_3$ is carboxy-$(C_1-C_6)$-alkyl, where the alkyl group is linear or branched and is unsubstituted or substituted by a monocyclic or bicyclic heteroaryl having 1–4 heteroatoms, or monosubstituted or polysubstituted by a phenyl ring, where said phenyl ring is unsubstituted or is monosubstituted or polysubstituted by halogen, $(C_1-C_6)$-alkyl, $(C_3-C_7)$-cycloalkyl, carboxyl groups, carboxyl groups esterified with linear or branched $(C_1-C_6)$-alkanols, carbamoyl groups, trifluoromethyl groups, hydroxyl groups, methoxy groups, ethoxy groups, benzyloxy groups or amino groups, which in turn are substituted by benzyl, benzoyl or acetyl; or
- $R_3$ is the acid radical of an amino acid selected from the group consisting of histidine, leucine, valine, serine (Bzl), threonine, pipecolic acid, piperidine-4-carboxylic acid, piperidine-3-carboxylic acid, ε-NH$_2$-lysine, ε-Z-NH-lysine, ε-(2Cl-Z)-NH-lysine, 2-pyridylalanine, phenylalanine, tryptophan, glutamic acid, arginine (Tos), asparagine, citrulline, homocitrulline, ornithine, proline, indoline-2-carboxylic acid, octahydroindolinecarboxylic acid, tetrahydroisoquinolinecarboxylic acid, 5-aminovaleric acid and 8-amino-octanoic acid, where the N terminus of the amino acids is unsubstituted or substituted by butoxycarbonyl, carboxybenzyl or the acid radical of mono-, bi- or tri-cyclic arylcarboxylic or heteroarylcarboxylic acids having 1–4 heteroatoms, or by carboxy-$(C_1-C_{12})$-alkyl, carboxycyclopentane, carboxycyclohexane or benzoyl, which may be unsubstituted or monosubstituted or polysubstituted by halogen, methoxy groups, amino groups, carbamoyl groups, trifluoromethyl groups, carboxyl groups or carboxyl groups esterified with linear or branched $(C_1-C_6)$-alkanols;
- $R_4$ is H, F or $OR_5$;
- $R_5$ is hydrogen, $(C_3-C_7)$-cycloalkyl, $(C_1-C_6)$-alkyl or carboxy-$(C_1-C_6)$-alkyl, where the alkyl group is linear or branched and is unsubstituted or substituted by a mono-, bi- or tri-cyclic carbonylaryl or carbonylheteroaryl having 1–4 heteroatoms, where aryl or heteroaryl itself is unsubstituted or is monosubstituted or polysubstituted by halogen, $(C_1-C_6)$-alkyl, $(C_3-C_7)$-cycloalkyl, carboxyl groups, carboxyl groups esterified with linear or branched $(C_1-C_6)$-alkanols, carbamoyl groups, trifluoromethyl groups, hydroxyl groups, methoxy groups, ethoxy groups, benzyloxy groups or amino groups, which in turn are substituted by benzyl, benzoyl or acetyl;
- A is an aromatic or non-aromatic carbon ring;
- B is $CH_2$ and D is CH; or
- B—D is CH=C;
- X is O, S or $H_2$; and
- Y is C or a single bond;

with the proviso that when $R_1$, $R_2$ and $R_3$ are all lower alkyl groups or hydrogen, B—D is CH=C.

2. The ligand of claim 1 wherein $R_1$ is a $(C_1-C_{12})$-alkyl group which is substituted by a monocyclic or bicyclic heteroaryl having 1–4 heteroatoms selected from the group consisting of N, S and O.

3. The ligand of claim 2 wherein said heteroaryl is morpholine, piperizine, piperidine, indole, indazole, phthalizine, thiophene, furan or imidazole.

4. The ligand of claim 1 wherein $R_2$ is a $(C_1-C_{12})$-alkyl group which is substituted by a monocyclic or bicyclic heteroaryl having 1–4 heteroatoms selected from the group consisting of N, S and O.

5. The ligand of claim 4 wherein said heteroaryl is morpholine, piperizine, piperidine, indole, indazole, phthalizine, thiophene, furan or imidazole.

6. The ligand of claim 1 wherein $R_3$ is a a carbonyl heteroaryl having 1–4 heteroatoms selected from the group consisting of N, S and O.

7. The ligand of claim 1 wherein $R_3$ is a carboxy-$(C_1-C_6)$-alkyl group which is substituted by a monocyclic or bicyclic heteroaryl having 1–4 heteroatoms selected from the group consisting of N, S and O.

8. The ligand of claim 7 wherein said heteroaryl is morpholine, piperizine, piperidine, indole, indazole, phthalizine, thiophene, furan or imidazole.

9. The ligand of claim 1 wherein $R_3$ is an acid radical of an amino acid which is substituted by a heteroarylcarboxylic acid having 1–4 heteroatoms selected from the group consisting of N, S and O.

10. The ligand of claim 9 wherein said heteroarylcarboxylic acid is selected from the group consisting of methoxyphenylacetic acid, naphthylacetic acid, pyridylacetic acid, quinazolinonylacetic acid, indozolylacetic acid, indolylglyoxylic acid, phenylglyoxylic acid, isobutylglyoxylic acid, and 2-aminothiazole-4-glyoxylic acid.

11. The ligand of claim 1 wherein $R_5$ is an alkyl group which is substituted with a carbonylheteroaryl having 1–4 heteroatoms selected from the group consisting of N, S and O.

12. N-[1-Boc-Piperidyl-4-carbonyl]indoline-2-(R,S)-carboxylic acid [S-(N-ε-Boc)lysine methyl ester]amide.

13. N-[Piperidyl-4-carbonyl]indoline-2-(R,S)-carboxylic acid [S-(ε-NH$_2$)lysine methyl ester]amide.

14. N-[1-Boc-Indoline-2-(R,S)-carbonyl]indoline-2-(R,S)-carboxylic acid [S-(N-ε-Boc)lysine methyl ester]amide.

15. N-[Indoline-2-(R,S)-carbonyl]indoline-2-(R,S)-carboxylic acid [S-(N-ε-NH$_2$)lysine methyl ester]amide.

16. N-[1-Boc-Indoline-2-(R,S)-carbonyl]indoline-2-(R,S)-carboxylic acid [S-(N-ε-Z)lysine methyl ester]amide.

17. 1-Boc-Indoline-2-(R,S)-carboxylic acid [S-(N-ε-Z)lysine methyl ester]amide.

18. 1-Boc-Indoline-2-(R,S)-carboxylic acid (S-phenylalanine methyl ester)amide.

19. N-Boc-Indoline-2-(R,S)-carboxylic acid 4-piperidylamide.

20. N-Boc-Indoline-2-(R,S)-carboxylic acid (piperazinoacetic acid morpholide)amide.

21. N-[1-Boc-Piperidyl-4-carbonyl]indoline-2-(R,S)-carboxylic acid (piperazinoacetic acid morpholide)amide.

22. N-[N'-(4-Methoxyphenylacetyl)piperidyl-4-carbonyl]indoline-2-(R,S)-carboxylic acid [S-(N-ε-Z)lysine methyl ester]amide.

23. A drug containing at least one compound according to one of claims 12 to 22 and 1 in addition to conventional excipients and/or diluents or adjuncts.

24. A process for the preparation of a drug, characterized in that a compound according to one of claims 12 to 22 and 1 is processed to pharmaceutical formulations with conventional pharmaceutical excipients or diluents or other adjuncts, or is converted to a form applicable in therapeutics.

25. A drug according to claim 23 in the form of uncoated or coated tablets, capsules, solutions or ampoules, suppositories, plasters or powder formulations suitable for use in inhalers.

26. A composition comprising a compound of one of claims 12 to 22 and 1 in a pharmaceutically acceptable carrier.

27. The composition according to claim 26 which has antiasthmatic and/or immunosuppressive activity.

28. A method of binding pathogenically active immunophilins in a fluid comprising adding a carrier-fixed form containing a compound according to one of claims 1 and 22 to said fluid.

* * * * *